(12) United States Patent
Salah et al.

(10) Patent No.: US 11,790,532 B2
(45) Date of Patent: Oct. 17, 2023

(54) METHOD FOR CUTTING A MODEL OF A DENTAL ARCH

(71) Applicant: DENTAL MONITORING, Paris (FR)

(72) Inventors: Philippe Salah, Paris (FR); Thomas Pellissard, Paris (FR); Guillaume Ghyselinck, Cantin (FR); Laurent Debraux, Paris (FR)

(73) Assignee: DENTAL MONITORING, Paris (FR)

( * ) Notice: Subject to any disclaimer, the term of this patent is extended or adjusted under 35 U.S.C. 154(b) by 361 days.

(21) Appl. No.: 17/259,519

(22) PCT Filed: Jul. 10, 2019

(86) PCT No.: PCT/EP2019/068564
§ 371 (c)(1),
(2) Date: Jan. 11, 2021

(87) PCT Pub. No.: WO2020/011866
PCT Pub. Date: Jan. 16, 2020

(65) Prior Publication Data
US 2021/0272281 A1 Sep. 2, 2021

(30) Foreign Application Priority Data

Jul. 13, 2018 (FR) ...................................... 1856502

(51) Int. Cl.
*G06T 7/00* (2017.01)
*G06T 7/11* (2017.01)
(Continued)

(52) U.S. Cl.
CPC ................ *G06T 7/11* (2017.01); *G06F 30/27* (2020.01); *G06T 7/0012* (2013.01); *G16H 50/50* (2018.01);
(Continued)

(58) Field of Classification Search
CPC ..................... G06T 7/11; G06T 7/0012; G06T 2207/20081; G06T 2207/20084;
(Continued)

(56) References Cited

U.S. PATENT DOCUMENTS

2013/0022255 A1* 1/2013 Chen .......................... G06T 7/12
382/173
2016/0220200 A1* 8/2016 Sandholm ............ A61B 5/7246
(Continued)

OTHER PUBLICATIONS

Evangelos Kalogerakis, et al., "3D Shape Segmentation with Projective Convolutional Networks", Nov. 13, 2017, https//arxiv.org/pdf/1612.02808. (Year: 2017).*
(Continued)

*Primary Examiner* — Van D Huynh
(74) *Attorney, Agent, or Firm* — Ronald M. Kachmarik; Cooper Legal Group LLC

(57) ABSTRACT

Method for cutting a three-dimensional model of a dental scene, or "scene model." The method includes acquiring a view of the scene model, called the "analysis view." The method includes analyzing the analysis view by a neural network in order to identify, in the analysis view, at least one elementary zone representing an element of the dental scene, and assigning a value to at least one attribute of the elementary zone. The method includes identifying a region of the scene model represented by the elementary zone on the analysis view, and assigning, in the region, a value to an attribute of the scene model in accordance with the value of the attribute of the elementary zone.

7 Claims, 5 Drawing Sheets a) acquiring a view of said scene model, called the "analysis view"

b) analyzing the analysis view by means of a neural network in order to identify, in said analysis view, at least one elementary zone representing an element of the dental scene, and assigning a value to at least one attribute of said elementary zone c) identifying a region of the scene model represented by said elementary zone on said analysis view, and assigning, in said region, a value to an attribute of said scene model in accordance with said value of said attribute of the elementary zone d) modifying the analysis view, then resuming at step b), e) grouping the regions of the scene model which have the same value for an attribute of said scene model, so as to create an elementary model.

(51) Int. Cl.
    *G16H 50/50*     (2018.01)
    *G06F 30/27*     (2020.01)
    *A61C 7/00*     (2006.01)
    *G06N 3/08*     (2023.01)

(52) U.S. Cl.
    CPC ............... *A61C 7/002* (2013.01); *G06N 3/08* (2013.01); *G06T 2207/20081* (2013.01); *G06T 2207/20084* (2013.01); *G06T 2207/30036* (2013.01); *G06V 2201/03* (2022.01)

(58) Field of Classification Search
    CPC .......... G06T 2207/30036; G06F 30/27; G16H 50/50; A61C 7/002; G06N 3/08; G06V 2201/03
    USPC .......................................................... 382/128
    See application file for complete search history.

(56) References Cited

U.S. PATENT DOCUMENTS

| | | | | |
|---|---|---|---|---|
| 2016/0275679 | A1* | 9/2016 | Im ........................ | G06T 11/003 |
| 2018/0028294 | A1* | 2/2018 | Azernikov ........ | G06F 18/24143 |
| 2018/0168781 | A1* | 6/2018 | Kopelman ............ | A61B 90/36 |
| 2018/0360567 | A1* | 12/2018 | Xue ...................... | A61C 7/002 |
| 2019/0231490 | A1* | 8/2019 | Sabina ................ | A61B 1/0646 |

OTHER PUBLICATIONS

International Search Report corresponding to International Application No. PCT/EP2019/068564 dated Aug. 6, 2019, 8 pages.
Zhige Xie, et al., "Projective Feature Learning for 3D Shapes with Multi-View Depth Images", Computer Graphics Forum, GB, vol. 34, No. 7, Oct. 1, 2015, pp. 1-11.
Evangelos Kalogerakis, et al., "3D Shape Segmentation with Projective Convolutional Networks", Nov. 13, 2017, https://arxiv.org/pdf/1612.02808.
Yunhai Wang, et al., "Projective analysis for 3D shape segmentation", ACM Transactions on Graphics (TOG), ACM, US, vol. 32, No. 6, Nov. 1, 2013, pp. 1-12.
Evan Shelhamer, et al., "Fully Convolutional Networks for Semantic Segmentation", May 20, 2016, https://arxiv.org/pdf/1605.06211.
Guo Kan, et al., "Image-guided 3D model labeling via multiview alignment" Graphical Models, Elsevier, San Diego, CA, US, vol. 96, Feb. 10, 2018, pp. 30-37.
Xiaojie Xu, et al., "3D Tooth Segmentation and Labeling using Deep Convolutional Neural Networks", IEEE Transactions on Visualization and Computer Graphics, US, May 22, 2018, pp. 1-13.

* cited by examiner

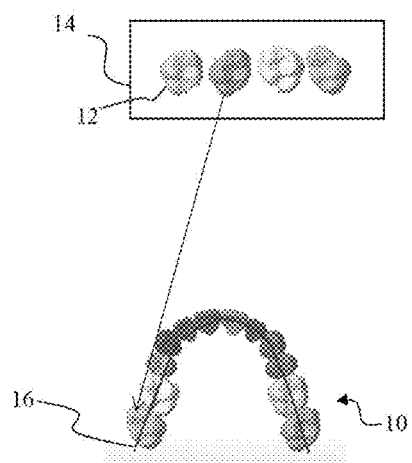
Fig. 5
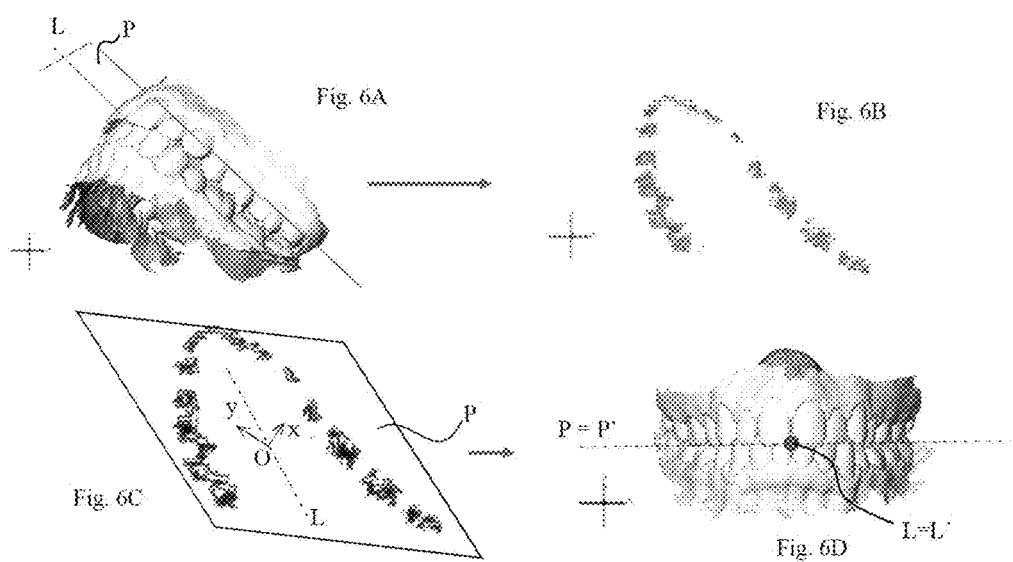
Fig. 6A
Fig. 6B
Fig. 6C
Fig. 6D

METHOD FOR CUTTING A MODEL OF A DENTAL ARCH

TECHNICAL FIELD

The present invention relates to a method for cutting a three-dimensional model of a dental arch.

BACKGROUND ART

The cutting of a three-dimensional model into elementary models is an operation by which the model is cut up in order to delimit the representation of one or more elements of the modeled scene. In particular, the applicant has invented several methods in which a model of a dental arch is cut up in order to define elementary models for each tooth, or "tooth models". The model thus cut up can then be deformed, by displacement of the tooth models, in order to simulate the effect of an orthodontic treatment, or the course of a recurrence, or a cosmetic treatment.

The cutting can be partially automated, particularly in order to define the contour of the teeth. However, the intervention of an operator is still needed in order to refine and validate the cutting, especially in order to take account of the context.

There is an ongoing need to speed up the operation of cutting a model of a dental arch.

An aim of the invention is to respond to this need.

SUMMARY OF THE INVENTION

The invention proposes a method for cutting a three-dimensional model of a scene or "scene model", in particular a dental scene, said method comprising the following steps:
a) acquiring a view of said scene model, called the "analysis view";
b) analyzing the analysis view by means of a trained neural network in order to identify, in said analysis view, at least one elementary zone representing an element of the scene, and determine a value for at least one attribute of the elementary zone;
c) identifying a region of the scene model corresponding to the elementary zone, that is to say represented by said elementary zone on said analysis view, and assigning, to said region, a value of an attribute of said scene model, or "model attribute", said value of the model attribute being dependent on the value of said attribute of the elementary zone.

As will be seen in more detail in the course of the description, a cutting method according to the invention utilizes the capacities of a neural network for the analysis of images, in this case views of the scene model, so as to enrich the description of this model. The method can be used in particular to identify, in the scene model, the regions whose nature has been identified, by the neural network, on the analysis view.

Preferably, the elementary zone defines the representation of a physical element of the scene, for example a tooth. The elementary zone is then designated as a "tooth zone".

The attribute of the elementary zone can be chosen in particular from a tooth number, a tooth type, a tooth shape parameter, an index of mesial and distal deflection of the incisal margin, a level of abrasion, a tooth appearance parameter, a parameter relating to the state of the tooth, or a parameter relating to a dental appliance carried by the tooth.

The model attribute can be identical to or different from the attribute of the elementary zone. Preferably, these two attributes are identical, and in particular they can be a number of the tooth.

Preferably, the method further comprises, after step c), the following step:
d) modifying the analysis view, then resuming at step b).

By multiplying the cycles of steps b) to d), it is thus possible to explore the scene model, that is to say to acquire numerous analysis views, under different observation conditions, and in particular at different orientations, so as to manage to assign values, for said model attribute, to all the voxels of said scene model.

Preferably, the method further comprises, after more than 10, more than 100 or more than 1,000 cycles of steps b) to d), the following step e):
e) grouping the regions of the scene model which have the same value for said model attribute, so as to create an elementary model.

For example, the scene model can be a model of a dental arch, or "arch model", and the attribute of the elementary zone can be a tooth number. Then, when the part of the arch model that represents a tooth is observed from different directions, the cycles of steps b) to d) make it possible to progressively identify all the voxels of the arch model that belong to the representation of this tooth, and thereby to define a tooth model without the intervention of an operator.

Preferably, the method further comprises, after step e), the following step:
f) displacement and/or deformation and/or suppression of the elementary model.

The displacement of the elementary models makes it possible in particular to simulate a dental situation, in particular an orthodontic situation, past or future.

In one embodiment, the scene model is composed of an assembly of base regions, traditionally triangular, and, when, at step c), a value is assigned to an attribute of the scene model, for a region that includes at least one voxel of a base region, said value is assigned to the whole of said base region.

For example, if it is identified, at step c), that a voxel is the representation of a tooth no. 4, the triangular region that includes this voxel is immediately considered as representing the tooth no. 4. The cutting of the scene model is advantageously greatly accelerated by this.

A method can further comprise one or more of the following optional features:
the analysis view acquired at step a) and/or one or more of the analysis views modified at step d), preferably the analysis view acquired at step a) and all the analysis views modified at step d), are base analysis views obtained according to the following steps:
1) determining a predetermined orientation of the scene model, called the "base orientation";
2) determining a set of different conditions of observation of the scene model positioned in said base orientation, called the "base observation conditions";
3) acquiring a set of base analysis views, each base analysis view being acquired under respective base observation conditions;
at step 2), the set of said base observation conditions is determined in such a way as to minimize the number of said base observation conditions and to maintain, at a value greater than a predetermined threshold, the ratio of the total surface area of the set of the elementary models, determined at step e), to the surface area of the scene model;

at step 2), the set of said base observation conditions is determined in such a way as to minimize the number of said base observation conditions and to maintain, at a value greater than a predetermined threshold, for each of the base scene models of a group of base scene models, the ratio of the total surface area of the set of elementary models, determined at step e), to the surface area of the scene model;

the group of base scene models comprises more than 10, preferably more than 100, preferably more than 1,000 base scene models, each base scene model modeling at least part of a dental arch of a respective patient;

the method comprises, at the end of step e), the step of assigning each of at least some of the orphan voxels of the scene model, preferably each of the orphan voxels, to the elementary models created at step e), an orphan voxel not being able to be assigned to more than one elementary model, an orphan voxel being a voxel that is not grouped within an elementary model at step e).

A method according to the invention is performed at least in part, preferably in its entirety, by computer. The invention thus also relates to:

a computer program comprising program code instructions for the execution of one or more of steps of a method according to the invention, in particular at least steps b) and c), when said program is executed by a computer, a data medium on which such a program is recorded, for example a memory or a CD-ROM.

Definitions

A "patient" is a person for whom a method according to the invention is carried out, irrespective of whether this person is or is not following a course of orthodontic treatment.

The "occlusal plane" is the plane which provides the best linear correlation with all the points of contact between the teeth of the upper arch, on the one hand, and the teeth of the lower arch, on the other hand.

The "median longitudinal plane" is the plane that is substantially vertical when the patient holds his or her head straight, which substantially symmetrically separates right and left parts of each arch. The median longitudinal axis is the axis that extends to the intersection of the occlusal plane and the median longitudinal plane.

A "dental situation" defines a set of characteristics relating to a dental arch of a patient at one instant, for example the position of the teeth, their shape, the position of an orthodontic appliance, etc., at that instant.

A "model" is understood as a digital three-dimensional model. A model is composed of a set of voxels. A "model of an arch" is a model representing at least part of a dental arch, preferably at least 2, preferably at least 3, preferably at least 4 teeth.

For the sake of clarity, a distinction is traditionally made between the "cutting" of a scene model into "elementary models" and the "segmentation" of an image, in particular a view of a scene model, into "elementary zones". The elementary models and the elementary zones are representations, in 3D and 2D respectively, of an element of a real scene, for example of a tooth.

An observation of a model, under defined observation conditions, in particular at a defined angle and a defined distance, is called a "view".

An "image" is a two-dimensional representation, formed by pixels, of a scene. A view is an example of an image.

A "scene" is composed of a set of elements that can be observed simultaneously. A "dental scene" is a scene comprising at least part of a dental arch.

A tooth attribute is an attribute whose value is specific to the teeth. Preferably, a value of a tooth attribute is assigned to each tooth zone of the view in question or to each tooth model of a dental arch model in question. A tooth attribute does not concern the view or the model in its entirety. Its value derives from characteristics of the tooth to which it refers.

A "view of an arch", "representation of an arch", "scan of an arch" or "model of an arch" is understood as a view, a representation, a scan or a model of all or part of said dental arch.

A "learning base" is a base of computer records that is adapted to train a neural network. Each record comprises an object, for example an image, and information concerning this object, or a "descriptor". A descriptor comprises values for attributes of the object. For example, an attribute of an image of a dental scene can serve to identify the numbers of the teeth represented. The attribute is then a "tooth number" and, for each tooth, the value of this attribute is the number of this tooth.

A "neural network" or "artificial neural network" is a set of artificial intelligence algorithms well known to a person skilled in the art.

In the present description, the qualifying terms "historical" or "analysis" are used for purposes of clarity.

For the sake of clarity, "zones" and "regions" designate the surfaces of an image and of a model, respectively. A differentiation is also made between a "descriptor", which describes the object of a record of a learning base and which in particular comprises attribute values of this object, and a "description", which describes a model. An "elementary descriptor" specifically describes an elementary zone. An "elementary description" specifically describes an elementary model.

"Comprising" or "having" are to be interpreted non-restrictively, unless indicated otherwise.

BRIEF DESCRIPTION OF THE FIGURES

Other features and advantages of the invention will become clear from reading the following detailed description and by examining the appended drawing, in which:

FIG. 5 shows, schematically, the various steps of a method for creating a dental scene model by assembly of base tooth models;

FIGS. 6A-6D illustrate the treatment carried out to determine the occlusal plane of the dental scene model from FIG. 2;

DETAILED DESCRIPTION

Figure 1:
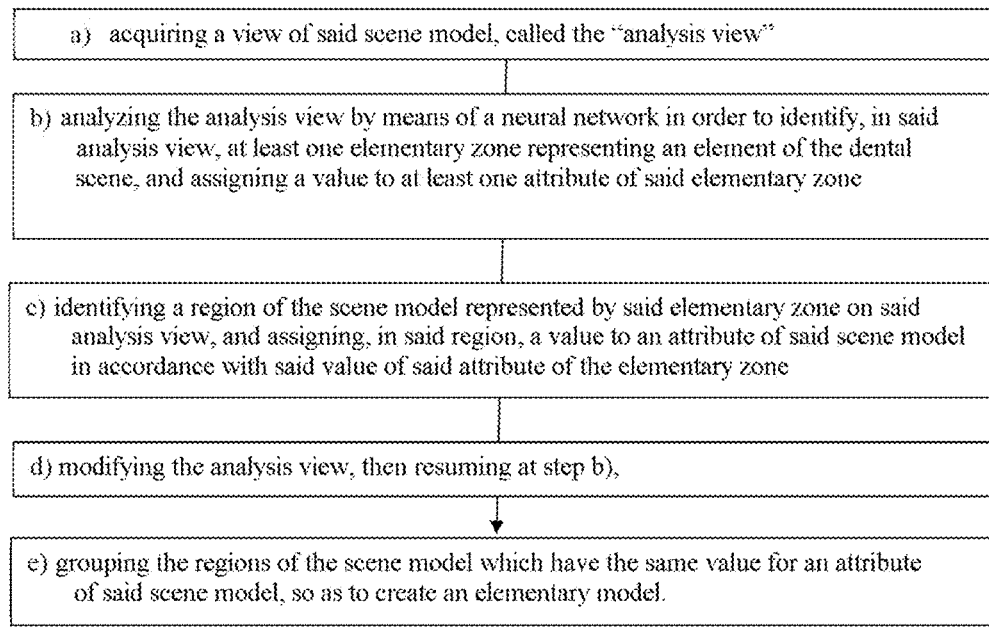
FIG. 1 shows, schematically, the various steps of a method according to the invention.

The following detailed description is that of preferred embodiments; it is not limiting in nature.

Creation of the Learning Base and Training of the Neural Network

Before step b) and preferably step a), a neural network must be trained with a learning base.

The learning base can be created according to conventional methods.

Traditionally, the learning base is composed of more than 1,000 "historical" records, each record comprising:
- a "historical" view of a "historical" digital three-dimensional model modeling a "historical" scene, in particular a dental arch of a "historical" patient;
- a "historical" descriptor of the historical view, a historical descriptor comprising a value for at least one attribute of a "historical" elementary zone representing, in the historical view, an element of the historical scene.

A historical model can be prepared from measurements carried out on the teeth of the historical patient or on an impression of his or her teeth, for example a plaster impression.

The historical model is preferably obtained from a real situation, preferably created using a 3D scanner.

In one embodiment, the historical model is theoretical, that is to say it does not correspond to a real situation. In particular, the historical model 10 (see FIG. 5) can be created by assembling a set of base tooth models 12 that are chosen from a digital library 14. The arrangement of the base tooth models is determined such that the historical model is realistic, that is to say corresponds to a situation that could be presented by a patient. In particular, the base tooth models are disposed along an arc 16, according to their nature, and are oriented in a realistic manner.

A historical model can be observed under different observation conditions in order to acquire different historical views.

Each historical view represents a set of historical elementary zones which each represent an element of the scene modeled by the historical model. This element can be a tooth.

For example, each record of the learning base can comprise a historical view of a dental arch and a descriptor containing for each tooth zone, that is to say for each elementary zone representing a tooth on the historical view, a value for at least one tooth attribute.

The tooth attribute is preferably chosen from a tooth number, a tooth type, a tooth shape parameter, for example a tooth with, in particular a mesio-palatal width, a thickness, a crown height, an index of mesial and distal deflection of the incisal margin, or a level of abrasion, an appearance parameter of the tooth, in particular a translucence index or a color parameter, or a parameter relating to the state of the tooth, for example "abraded", "broken", "decayed" or "fitted" (that is to say in contact with a dental appliance, for example an orthodontic appliance).

For example, the tooth attribute "tooth type" will have the value "incisor", "canine" or "molar" depending on whether the elementary zone represents an incisor, a canine or a molar, respectively. The tooth attribute "pathological situation" will have the value "healthy tooth", "broken tooth", "worn tooth" or "decayed tooth", for example.

The tooth attribute can also relate to an interaction between a dental appliance and the tooth in question. The tooth attribute can be, for example, "bonding on a tooth" and can assume the value "bonded" or "unbonded".

A historical view can also represent historical elementary zones, which each represent a different element of a tooth. In particular, on the basis of the historical model, it is possible to define elementary zones other than the tooth zones, and in particular models for the tongue and/or the mouth and/or the lips and/or the jaws and/or the gums and/or a dental appliance, preferably an orthodontic appliance, and to assign to them values for tongue and/or mouth and/or lips and/or jaws and/or gums and/or dental appliance attributes, respectively.

A tongue attribute can relate, for example, to the position of the tongue (for example assuming the value "set back").

A mouth attribute can relate, for example, to the extent to which the patient's mouth is open (for example assuming the value "mouth opened" or "mouth closed").

A dental appliance attribute can relate, for example, to the presence of a dental appliance and/or can relate to the state of the latter (for example assuming the value "appliance intact", "appliance broken" or "appliance damaged").

Traditionally, the historical descriptors are generated by an operator who, using a computer, delimits the elementary zones, preferably at least the tooth zones, and who, having identified a value of at least one attribute of an elementary zone, for example the nature of a tooth represented, for example "upper right canine", assigns this value to said attribute. This operation is called "labeling".

The generation of a historical descriptor can also be automatic, at least in part.

In particular, a description of the historical model is preferably generated, after which the historical descriptor is created, at least in part, on the basis of the description of the historical model.

To this end, the historical model is preferably cut up into historical elementary models and then, in the description of the historical model, a specific elementary description is generated for each historical elementary model.

In a preferred embodiment, the form of a historical elementary model, for example the form of a particular tooth model, is analyzed by means of a neural network trained to define a value for at least one attribute, for example a tooth number.

The description of a historical model thus comprises a set of data relating to the historical elementary models, for example to the historical elementary models that model the teeth, and preferably data relating to the historical model as a whole.

It is then possible to include, in the historical descriptor of a historical view, a historical elementary descriptor for each representation of a historical elementary model on the historical view, at least part of the historical elementary descriptor being inherited from the historical elementary description specific to the historical elementary model.

A historical elementary model can in particular model a tooth, and one or more tooth attributes can be associated with this historical elementary model. These tooth attributes can be chosen in particular from the tooth attributes listed above for the tooth zones.

For example, historical elementary models representing the teeth, or "historical tooth models", are created in the historical model, and, in the description of the historical model, a historical elementary description is created that is specific for each historical tooth model, for example in order to identify the corresponding tooth numbers. It is then easily possible to inform the historical descriptor, and in particular the historical elementary descriptors. In particular, the tooth numbers of the historical tooth models can be assigned to the representations of these historical tooth models on the historical view. Advantageously, once the historical model and its description have been created, it is thus possible to generate historical records by computer, without human intervention. The creation of the historical descriptor can then be at least partially automated. The risk of error is thereby advantageously limited.

In addition, this method makes it possible, by modifying the historical view of a given historical model, to generate a large number of historical records. Preferably, after a historical record has been generated, the historical view of the given historical model is modified, and then a new historical record is created.

In one embodiment, the historical model is deformed, for example by displacement of one or more tooth models, and new historical records are then generated using historical views of the deformed historical model. Advantageously, it then becomes possible to create different historical models which are not exclusively obtained from measurements performed on a patient, in particular from a scan of the dental arch of the patient. The historical models can be created in particular in order to simulate dental situations for which little actual data is available, for example situations relating to rare pathologies.

The neural network can be chosen in particular from:
the networks specialized in the classification of images, called CNN (convolutional neural network), for example—
AlexNet (2012)
ZF Net (2013)
VGG Net (2014)
GoogleNet (2015)
Microsoft ResNet (2015)
Caffe: BAIR Reference CaffeNet, BAIR AlexNet
Torch:VGG_CNN_S,VGG_CNN_M, VGG_CNN_M_2048,VGG_CN N_M_1024, VGG_CNN_M_128,VGG_CNN_F,VGG ILSVRC-2014 16-layer,VGG ILSVRC-2014 19-layer, Network-in-Network (Imagenet & CIFAR-10)
Google: Inception (V3, V4);
the networks specialized in the localization and detection of objects in an image, the Object Detection Network, for example:
R-CNN (2013)
SSD (Single Shot MultiBox Detector Object Detection network), Faster R-CNN (Faster Region-based Convolutional Network method: Object Detection network)—
Faster R-CNN (2015)
SSD (2015).
The above list is not exhaustive.

To be operational, the neural network must be trained by what is called a "deep learning" process, using the learning base.

By presenting the records of the learning base at the input of the neural network, the latter learns progressively how to segment an analysis view presented to it, that is to say how to analyze it and generate a descriptor making it possible to identify and class elementary zones of this view. In particular, the neural network learns to identify the representations of the teeth, on an analysis view of a dental arch, and to attribute to them corresponding attribute values.

The quality of the analysis performed by the neural network trained with the learning base depends directly on the number of records of the learning base. Preferably, the learning base comprises more than 5,000, preferably more than 10,000, preferably more than 30,000, preferably more than 50,000, preferably more than 100,000 records. The greater the number of records, the better the analysis capacity of the neural network.

Cutting of a Model

Figure 2:
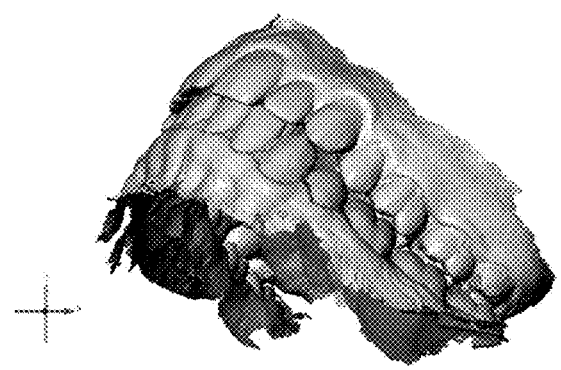
FIG. 2 shows an example of a model of a dental arch, that is to say of a dental scene model.

The scene model models a scene and in particular can model a dental scene of a patient (FIG. 2). It can be produced using the techniques described above for the generation of a historical model, and in particular by scanning a dental arch of a patient.

In order to cut a scene model, the procedure according to steps a) to c) is followed (FIG. 1), after the learning base has been created and the neural network has been trained.

At step a), a view of the scene model, or "analysis view", is acquired. The analysis view thus represents the scene model as observed under defined observation conditions. For example, an analysis view can represent the scene model viewed from the front. The analysis view contains elementary zones which each represent an element of the modeled scene. For example, if the analysis view is a front view, it can comprise a representation for the right incisor, a representation for the left incisor, and a representation for the gum. These representations each constitute an elementary zone.

At step b), the analysis view is presented to the trained neural network. The neural network analyzes the analysis view and determines values for attributes of the elementary zones. Thus, the neural network determines a descriptor for the analysis view. In particular, it can determine, with a probability, the contours of the elementary zones and the nature of the elements represented by these elementary zones. For example, it can determine with a probability of 95% that an elementary zone at the center of the analysis view is an incisor. Trials have shown that a neural network is well suited for analyzing a view of a dental model.

At step c), one identifies, for each elementary zone determined at step b), the region of the scene model from which it derives.

A view of an arch model is always unique, which is to say that it can only be acquired under specific observation conditions. Particular observation conditions thus apply bijectively to an analysis view. With the observation conditions that permitted acquisition of the analysis view being known, it is possible to deduce, for each elementary zone, one and only one region of the scene model, called the "parent region", which, when observed under the observation conditions, is represented by the elementary zone.

Values of the descriptor of the analysis view, and in particular the attribute values that are specific to the elementary zone, can then be assigned to the parent region.

For example, if an attribute value of an elementary zone indicates that "the elementary zone is an at least partial representation of an incisor", the voxel of the scene model which is represented on the analysis view by a pixel belonging to the elementary zone can inherit this attribute value and be considered as belonging also "to the representation of an incisor", that is to say as belonging to an elementary model of a incisor. It can also be said that the voxel is "assigned" to the elementary model representing the incisor.

The resolution of the scene model being limited, this model is traditionally an assembly of base regions of triangular shape, or "triangles", of different sizes. Where an attribute value is assigned to a region of the scene model that contains at least one voxel of a triangle, said region can be extended to include the whole triangle. The cutting of the scene model is thereby accelerated.

At the end of step c), essentially only the parent regions of elementary zones of the analysis view have a description specifying an attribute value deduced from the analysis of the analysis view.

At step d), the analysis view is therefore modified, which is to say that the observation conditions of the scene model are modified, and then steps b) and c) are resumed. The analysis view having been modified, the same applies to the elementary zones and corresponding parent regions.

The cycle of steps b) to d) is preferably resumed, for example more than 10 times, more than 100 times or more than 1,000 times, preferably turning around the scene model. Preferably, the cycle of steps b) to d) is repeated until all of the identified parent regions having inherited attribute values of elementary zones represent more than 50%, preferably more than 60%, more than 70%, more than 80%, more than 90%, preferably substantially 100% of the surface of the scene model.

At the end of step d), the parent regions that share the same value for an attribute, for example the regions that are all considered as "belonging to the upper right incisor", can be grouped in order to form an elementary model, for example an elementary model of an upper right incisor.

The method thus makes it possible to cut a scene model, and in particular to cut a dental arch model, in order to create elementary models, especially for the teeth of the arch model.

The scene model that has been cut can be used in all applications in which cut scene models are used at present. In particular, the cut scene model can be used to simulate an orthodontic treatment or to design an orthodontic appliance, for therapeutic purposes or for non-therapeutic purposes, for example for research purposes or purely cosmetic purposes.

Example

Figure 3:
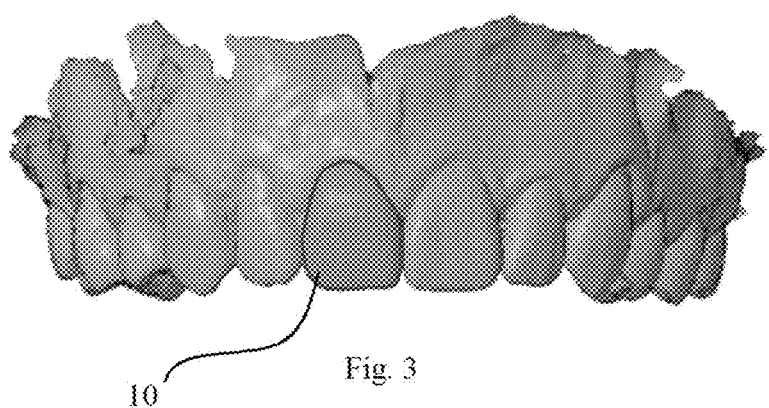
FIG. 3 shows an example of an "analysis view" of a model of a dental arch.

FIG. 3 is an analysis view of a dental arch. The neural network has made it possible to identify, on this view, representations of different elements of the dental scene, and in particular it has made it possible to identify elementary zones that are representations of teeth and of the gums. It has identified in particular that the elementary zone 10 is the representations of an incisor. The value of the attribute "tooth type" of the elementary zone 10 is therefore "incisor".

Figure 4:
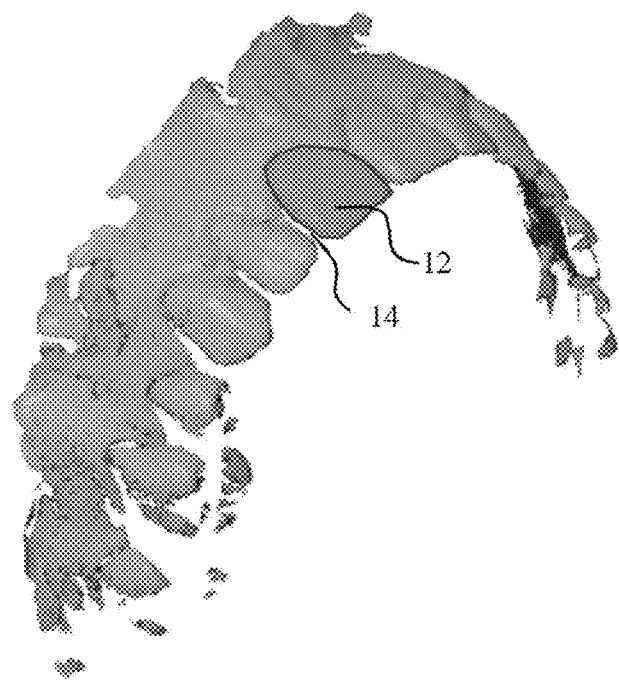
FIG. 4 shows the regions of said dental arch model that are "parents" of the elementary zones identified on the analysis view shown in FIG. 3.

At step c), the parent regions of the different elementary zones have been identified in the model represented on the analysis view. FIG. 4 shows these different parent regions. In particular, the region 12 is parent of the elementary zone 10. It is thus possible to conclude that the region 12 of the model is a region which represents, at least in part, an incisor. The value of the "tooth type" model attribute of the region 12 is therefore "incisor".

It will be noted that FIG. 4 is incomplete. The parts of the model that are not visible on the analysis view have not been identified. For example, the parts that extend between the incisor and the adjacent canine have not been identified, which leaves an empty space 14 in FIG. 4.

In order to identify the nature of these parts, for example in order to determine, in the empty space 14, the model surfaces that belong to the gum, to the incisor and to the adjacent canine, one or more other analysis views representing the part of the model corresponding to the empty space 14 have to be acquired and then subjected to the neural network.

The cycle between steps b) and d) thus makes it possible to identify all the surfaces of the incisor that are represented on the model. The model can thus be cut automatically.

Improvement

In order to cut a scene model precisely into elementary models, it is preferable to multiply the cycles of steps b) to d), preferably to carry out more than 1,000 cycles, preferably turning around the scene model. This procedure takes a long time. There is a need to speed it up.

Pursuing their research, the inventors have discovered a solution by which it is possible to meet this need without compromising on precision. More specifically, they propose an "improved" cutting method comprising the following steps:
1) determining a spatial orientation of the scene model, called the "base orientation";
2) determining a set of different conditions of observation of the scene model positioned in said base orientation, called "base observation conditions";
3) acquiring a set of analysis views called "base analysis views", each base analysis view being acquired under respective base observation conditions;
4) implementing the cutting method comprising steps a) to e) for each of the base analysis views.

In other words, at step 4), the analysis views analyzed during the different occurrences of step b), that is to say the analysis view from step a), then the modified analysis views from successive steps d), are formed each time by a different base analysis view, the cutting method according to the invention being implemented as many times as is necessary so that all the base analysis views have been used.

As will be seen in more detail from the description below, the orientation of the scene model makes it possible to considerably limit the number of cycles while maintaining a good resolution of the elementary models. Unexpectedly, with scene models representing dental arch models, the inventors have achieved a degree of precision of greater than 95%, using fewer than 20 base analysis views.

At step 1), the scene model is a dental scene of one dental arch or both dental arches of a patient.

Preferably, as is shown in FIG. 6D, the scene model is oriented spatially in order to bring
the occlusal plane P of the scene model into coincidence with a predetermined reference plane P', and
the medial longitudinal axis L of the scene model, which extends in the occlusal plane P of said model, into coincidence with a predetermined reference axis L' which extends in the reference plane.

The occlusal plane and the median longitudinal axis of the scene model can be determined manually, in an approximate manner They are preferably determined by data processing.

Preferably, the scene model is a model of the dental arches with the mouth closed, that is to say in a position in which teeth of the upper arch are in contact with teeth of the lower arch (FIG. 6A).

Traditionally, the dental scene model supplied by a three-dimensional scan makes it possible to differentiate the upper arch and the lower arch. Generally, the model is supplied in the form of two files corresponding respectively to these arches and comprising data allowing the models of these arches to be positioned with respect to each other in the occlusion position.

In one embodiment, the dental scene model represents the two dental arches, and an occlusal plane is determined according to the following operations:
I. determining the points of the dental scene model which belong to an arch and which are at a distance from the other arch that is less than a predetermined distance from the other arch, called "contact points";

II. optionally filtering some of the contact points, preferably in such a way that the number of contact points belonging to the upper arch is identical to the number of contact points belonging to the lower arch, preferably eliminating the points of an arch that are farthest from the other arch;

III. linear regression, preferably by the least squares method, over all the points of contact remaining, so as to determine the occlusal plane.

At step I, to estimate the contact points between the teeth of the upper and lower arches (FIG. 6A), the set of the points of the model of the upper arch and of the lower arch which are at a distance less than a predetermined limit is preferably determined, this limit preferably being less than 3 mm, preferably approximately 2 mm All the other points of these models are then disregarded, which results in the representation of FIG. 6B.

At step II, contact points of the arch that comprises more of them are suppressed until the number of contact points is identical for both arches. The precision of the linear regression at step III is thereby improved.

At step III, a conventional linear regression then permits determination of the occlusal plane (reference sign "P" in FIG. 6C).

The dental scene model can then be oriented by modifying the orientation of the occlusal plane (FIG. 6D), for example by disposing the occlusal plane P horizontally if the reference plane P' is horizontal.

If the dental scene model does not comprise data making it possible to position the upper and lower arches relative to each other, a check-bite is preferably used, revealing the points of contact between the upper teeth and the lower teeth, then the models of the arches are repositioned in relation to this check-bite.

To determine the orientation of the scene model in the occlusal plane, it is necessary to orient the median longitudinal axis L with a reference axis L' of the occlusal plane.

Preferably, the following operations are conducted:
i. projecting, into an occlusal plane of the dental scene model, contact points between the teeth of the patient's upper arch and lower arch, the contact points and/or the occlusal plane preferably being determined according to steps I to III;
ii. determining the barycenter of the projections of said contact points and creating a reference frame, in the occlusal plane, centered on said barycenter;
iii. determining, in said reference frame, the parabolic function having the highest coefficient of correlation with all of the projections of the contact points;
iv. rotating all of the projections of the contact points around the barycenter, and repeating the preceding operation iii until all of the projections of the contact points have run through a determined sector, preferably greater than 90°, greater than 180°, or even around 360°;
v. identifying the highest coefficient of correlation for all of the angular positions of all of the projections of the contact points around the barycenter, and the axis of the corresponding parabolic function;
vi. determining the median longitudinal axis of the scene model as being said axis of the parabolic function.

At step ii., axes [Ox) and [Oy) are considered in the occlusal plane (FIG. 6C), the point O being the barycenter of the normal projections of the points of contact on the occlusal plane P.

At step iii., this reference frame (xOy) is searched for the curve, preferably parabolic, which exhibits the greatest coefficient of correlation with the set of said projections At step iv., the set of the projections of the contact points is then moved in the occlusal plane, by rotation about the point O, and the preceding step is recommenced from this new angular position of the projections of the contact points.

The cycle of the above operations is continued, preferably until all of the contact points have been rotated by 360° about the barycenter 0. The coefficients of correlation corresponding to the different orientations of the set of contact points are then compared.

At steps v. and vi., the axis of the curve which leads to the highest coefficient of correlation is considered as being the median longitudinal axis (reference sign "L" in FIG. 6C).

The dental scene model can then be oriented by modifying the orientation in the occlusal plane (FIG. 6D), by aligning the median longitudinal axis L with the reference axis L'.

The "base" orientation of the scene model in space (FIG. 6D) can thus be perfectly determined, rapidly, by computer.

Of course, the spatial orientation of the dental scene model can be effected by other methods, for example by means of a neural network trained for this purpose.

At step 2), a set composed of different observation conditions for the scene model positioned in said base orientation is determined, called "base observation conditions". This set is called the "observation configuration".

In order to acquire a base analysis view, a virtual acquisition appliance V is positioned under respective base observation conditions.

Figure 7:
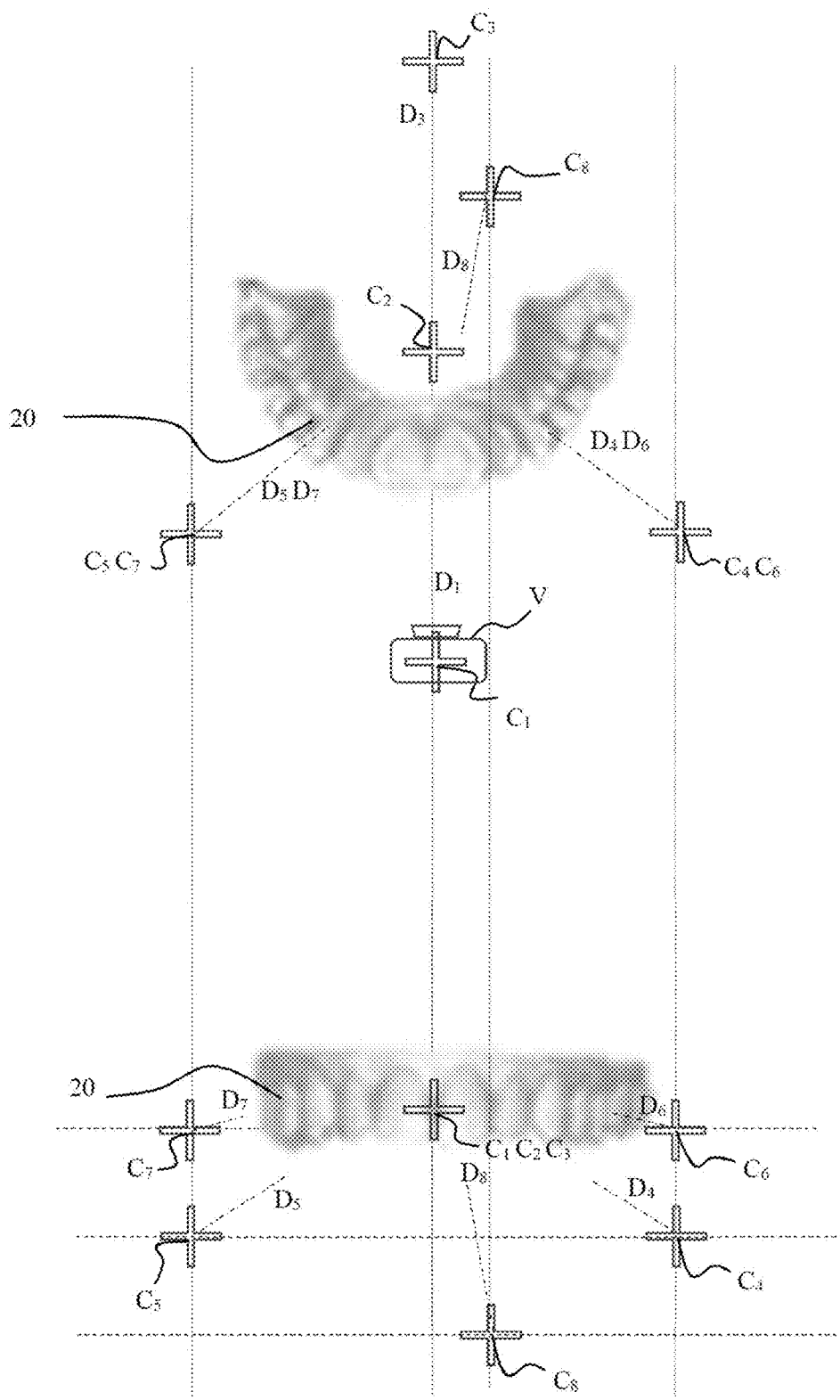
FIG. 7 illustrates an example of a set of base observation conditions for a dental scene model.

FIG. 7 illustrates an example of an observation configuration comprising 8 base observation conditions for a scene model 20. To each base observation condition there is assigned
- a different observation position $C_i$, represented by a cross, and
- a direction of observation $D_i$ of the scene model, for the virtual acquisition appliance V intended for the acquisition of the corresponding base analysis view,
- i being between 1 and 8.

The determination of the observation configuration can be effected manually, by testing different observation configurations.

Preferably, the observation configuration is determined in such a way as to minimize the number of base observation conditions. Preferably, the overlap between the different base analysis views that are obtained with the observation configuration are minimized To put it another way, the observation configuration is determined such that the surface of the scene model represented on more than one base analysis view is minimal.

The observation configuration is preferably determined according to the elementary models that are to be created. For example, in order to model the teeth, it is preferable that the observation configuration does not contain an analysis view that does not represent at least one tooth.

The term "degree of precision" signifies the percentage of the surface of the scene model which, at the end of step e) of step 4), has been assigned to an elementary model. It is in fact possible that all the regions of the scene model that are represented by elementary zones on the different base analysis views used do not suffice to cover the whole surface of the scene model.

Preferably, at step 2), the observation configuration is determined according to a minimal degree of precision that is to be reached for the elementary models. Preferably, the observation configuration is determined in such a way that the degree of precision is greater than 90%, preferably greater than 95%, even greater than 98%.

Preferably, at step 2), the observation configuration is determined in such a way as to minimize the number of base observation conditions, while obtaining elementary models that have a degree of precision greater than a minimal degree of precision.

At step 3), the analysis views, called "base analysis views", are acquired, observing the dental scene model under the base observation conditions.

Figure 8:
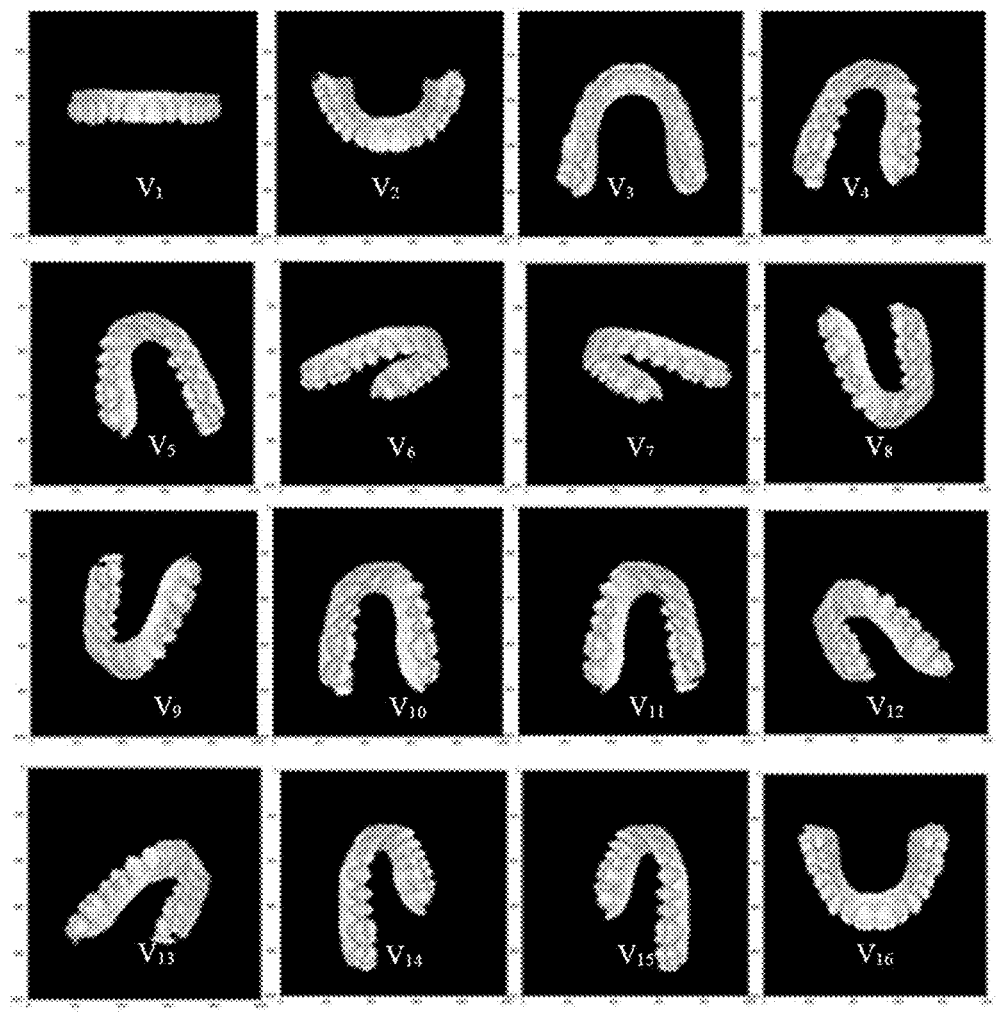
FIG. 8 illustrates an example of a set of base analysis views of a dental scene model, this set being obtained from an observation configuration grouping 16 base observation conditions.

FIG. 8 illustrates a set of base analysis views $V_i$, i being between 1 and 16, corresponding to an example of an observation configuration. The first 8 base analysis views $V_i$ correspond substantially to the base observation conditions illustrated in FIG. 7.

Step 3) can be carried out completely prior to step 4), or progressively, during the implementation of the cutting method according to the invention, as the base analysis views are used.

At step 4), the base analysis views are used to implement the cutting method according to the invention.

For example, at step a), the base analysis view $V_1$ is used, after which 7 cycles of steps a) to d) are effected with the base analysis views $V_2$ to $V_8$, and then a step e) is carried out.

Surprisingly, cutting of high quality is possible with a limited number of base analysis views, in particular with fewer than 50, fewer than 30, fewer than 20 or fewer than 15 base analysis views. The cutting method is thus greatly accelerated.

Nonetheless, the degree of precision remains very high. With the set of base analysis views of FIG. 8, it exceeds 98%.

Preferably, the improved cutting method also comprises, at the end of step 4), the following step:
5) assigning each of at least some of the orphan voxels of the scene model, preferably each of the orphan voxels, to the elementary models created at step e), an orphan voxel not being able to be assigned to more than one elementary model.

An "orphan" voxel is a voxel that is not grouped within an elementary model at step e). For example, if the degree of precision is 95%, the voxels constituting the complementary 5% of the scene model are orphan voxels.

The rules of assigning an orphan voxel to an elementary model depend on the object modeled by the elementary model. For example, an orphan voxel can be assigned to the nearest elementary model.

In a preferred embodiment, the observation condition is determined at step 2) in such a way as to minimize the number of base observation conditions in said observation configuration, while obtaining, at the end of step 4), elementary models that have a degree of precision that is greater than a predetermined threshold, preferably a minimal degree of precision, for each "base" scene model of a group comprising more than 10, more than 100, preferably more than 1,000 different base scene models.

Advantageously, the observation configuration thus determined is adapted to numerous scene models called "base scene models". If the group comprises a sample of base scene models that is representative of the dental arches of a population, the observation configuration may advantageously be suitable for any given scene model, that is to say for any patient of this population.

Of course, the invention is not limited to the embodiments described above and shown.

In particular, the patient is not limited to a human being. A method according to the invention can be used for another animal.

The invention claimed is:

1. A method for cutting a three-dimensional model of a dental scene, or "scene model", said method comprising the following steps:
    a) acquiring a view of said scene model, called the "analysis view";
    b) analyzing the analysis view by means of a trained neural network in order to
        identify, in said analysis view, at least one elementary zone representing an element of the dental scene, and
        determine a value for at least one attribute of said elementary zone;
    c) identifying a region of the scene model represented by said elementary zone on said analysis view, and assigning, to said region, a value of an attribute of said scene model, or "model attribute", said value of the model attribute being dependent on the value of said attribute of the elementary zone,
    d) modifying the analysis view, then resuming at step b), the method comprising, after more than 10 cycles of steps b) to d), the following step:
    e) grouping the regions of the scene model which have the same value for an attribute of said scene model, so as to create an elementary model;
in which the analysis view acquired at step a) and/or one or more of the analysis views modified at step d), are base analysis views obtained according to the following steps:
    1) determining a predetermined orientation of the scene model, called the "base orientation";
    2) determining a set of different conditions of observation of the scene model positioned in said base orientation, called "base observation conditions", the set of said base observation conditions is determined in such a way as to minimize the number of said base observation conditions and to maintain at a value greater than a predetermined threshold, for each of the base scene models of a group of base scene models, the ratio of the total surface area of the set of the elementary models, determined at step e), to the surface area of the scene model:
    3) acquiring a set of base analysis views, each base analysis view being acquired under respective base observation conditions.

2. The method as claimed in claim 1, in which the analysis view acquired at step a) and all the analysis views modified at step d) are base analysis views obtained according to steps 1), 2), 3).

3. The method as claimed in claim 1, in which said group of base scene models comprises more than 10, preferably more than 100, preferably more than 1,000 base scene models, each base scene model modeling at least part of a dental arch of a respective patient.

4. The method as claimed in 1, comprising, at the end of step e), the step of assigning each of at least some of the orphan voxels of the scene model, preferably each of the orphan voxels, to the elementary models created at step e), an orphan voxel not being able to be assigned to more than one elementary model, an orphan voxel being a voxel that is not grouped within an elementary model at step e).

5. The method as claimed in 1, in which, at step c), the attribute of said scene model is identical to the attribute of the elementary zone.

6. The method as claimed in 1, in which, at step b), the attribute of the elementary zone is chosen from a tooth number, a tooth type, a tooth shape parameter, an index of mesial and distal deflection of the incisal margin, or a level of abrasion, a tooth appearance parameter, a parameter relating to the state of the tooth, and a parameter relating to a dental appliance carried by the tooth.

7. The method as claimed in claim 6, in which the attribute of the elementary zone is chosen from a tooth number and a tooth type.

\* \* \* \* \*